United States Patent [19]

Masuho et al.

[11] Patent Number: 4,638,049

[45] Date of Patent: Jan. 20, 1987

[54] ANTITUMOR PROTEIN HYBRID AND PROCESS FOR THE PREPARATION THEREOF

[75] Inventors: Yasuhiko Masuho, Hino; Takeshi Hara, Hachioji; Teruhisa Noguchi, Fujisawa, all of Japan

[73] Assignee: Teijin Limited, Osaka, Japan

[21] Appl. No.: 137,193

[22] Filed: Apr. 4, 1980

[30] Foreign Application Priority Data

Apr. 9, 1979 [JP] Japan .................................. 54-41919

[51] Int. Cl.$^4$ ........................................... C07K 15/14
[52] U.S. Cl. .................................................... 530/388
[58] Field of Search ......................................... 530/388

[56] References Cited

U.S. PATENT DOCUMENTS

| | | | |
|---|---|---|---|
| 4,160,018 | 7/1979 | Bjorklund | 260/112.5 R |
| 4,160,019 | 7/1979 | Bjorklund | 260/112.5 R |
| 4,174,385 | 11/1979 | Reid | 260/112.5 R |
| 4,201,770 | 5/1980 | Stevens | 260/112.5 R |

*Primary Examiner*—Delbert R. Phillips

*Attorney, Agent, or Firm*—Sughrue, Mion, Zinn, Macpeak, and Seas

[57] ABSTRACT

Antitumor protein hybrid, composed of a moiety which is substantially the fragment Fab of an antitumor immunoglobulin and a moiety which is substantially the fragment A of a diphtheria toxin, which is expressed by the following formula (I):

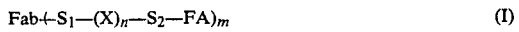

$$\text{Fab} + S_1 - (X)_n - S_2 - \text{FA})_m \qquad (I)$$

(where Fab indicates a moiety which is substantially the fragment Fab of an antitumor immunoglobulin; FA indicates a moiety which is substantially the fragment A of a diphtheria toxin; X indicates a divalent organic radical; $S_1$ and $S_2$ are both sulfur atoms, $S_1$ indicating a sulfur atom arising from the disulfide bond (—S—S— bond) in an immunoglobulin and $S_2$ a sulfur atom arising from the disulfide bond in a diphtheria toxin; n stands for 0 to 1 and m stands for an integer of 1 to 5). This antitumor protein hybrid has remarkable and specific cytotoxicity against tumor cells, e.g., in mice.

9 Claims, 10 Drawing Figures

FRAGMENT A     FRAGMENT B

ANTITUMOR PROTEIN HYBRID AND PROCESS FOR THE PREPARATION THEREOF

BACKGROUND OF THE INVENTION

1. Field of the Invention

The present invention relates to a novel antitumor protein hybrid, for example, cytotoxic against mouse tumors and a process for the preparation thereof. More particularly, the present invention relates to a novel protein, which, having a moiety which is substantially the fragment Fab of an antitumor immunoglobulin and a moiety which is substantially the fragment A of a diphtheria toxin, is specifically useful as a remedy for malignant tumor, e.g., in mice, and a process for the preparation of the same.

2. Description of the Prior Art

As for the remedies for malignant tumor or cancer (antitumor agents), many drugs have hitherto been known; however, these drugs have a disadvantage that they can not be administered enough to destroy tumor cells, because they have a toxic effect not only upon tumor cells but also upon normal cells to a considerable degree. Several attempts have been made to overcome such this disadvantage by combining an antitumor agent or a protein toxin which is cytotoxic with a specific carrier in order to have them selectively absorbed by tumor cells. There exists an antitumor antibody (antitumor immunoglobulin), though very small in amount, in the blood of a cancer patient or on the surface of tumor cells. An antitumor antibody can also be obtained by immunizing an animal with the tumor cells and absorbing the obtained antiserum with human normal cells. Antitumor antibodies, whether autochthonus, allogeneic, or xenogeneic, are not always capable of displaying a cytotoxic effect against tumor cells; however, they have a common nature of combining with tumor cells with an extremely high selectivity. Antitumor antibodies, therefore, have been used as a carrier to have an antitumor agent or a protein toxin absorbed by tumor cells selectively.

For instance, U.S. Pat. No. 4,093,607 (corresponding to G.B. No. 1,523,980 and F.R. No. 2,312,259) discloses, as an antitumor drug, a conjugate of antibody and antitumor drug in which such an antitumor drug as daunomycin, etc. is bound covalently with Fab' dimer of antitumor immunoglobulin. This is superior in that it carries the antitumor drug selectively to the target tumor cells; however, since an antitumor drug such as daunomycin, etc. bound with the antibody (Fab' dimer) exerts cytotoxic effects not only against tumor cells but also against normal cells, it is not satisfactory in view of destroying tumor cells only, and its cytotoxicity itself is not always sufficient either.

Studies have also been made to use diphtheria toxin, which is one of the protein toxins having much stronger toxicity, in the place of an antitumor drug.

For instance, F. L. Moolten et al. report that they prepared a conjugate by conjugating rabbit's anti-SV40-transformed hamster sarcoma or lymphoma antibody to diphtheria toxin with glutaraldehyde as a coupling agent and were able to protect hamsters challenged with SV40-transformed tumors by administering the conjugate to hamsters (Journal of the National Cancer Institute, vol. 55, pp 473–477, 1975).

P. E. Thorpe et al. report that the conjugate prepared by coupling diphtheria toxin to antilymphocytic antibody by means of chlorambucil greatly reduced the protein synthesis of human lymphoblastoid cells, CLA4. (Nature, vol. 271, pp 752–754, 1978). The results of these studies show that a conjugate of diphtheria toxin and antibody displays toxicity against the tumor cells selectively. However, these conjugates, when used as an antitumor drug, are believed to have some disadvantages as cited below. First, henogeneic antibody (immunoglobulin) has a strong antigenicity in the human body and induces the formation of anti-xenogeneic immunoglobulic antibody which deactivates the antitumor activity and further causes an anaphylaxis shock. The second of the disadvantages is that the non-specific toxicity of diphtheria toxin is not nullified. More particularly, the object of these methods is to conjugate diphtheria toxin on the surface of tumor cells by the aid of antitumor antibody; however, since the conjugate contains the whole molecule of diphtheria toxin in its composition, it tends to bind with normal cell surface receptors for diphtheria toxin and display cytotoxicity against normal cells. Thirdly comes the defect which is found in the method of cross-linking the antibody with the diphtheria toxin. Many of the cross-linking agents such as glutaraldehyde, toluene diisocyanate, chlorambucil, etc. effect the cross-linking not only between the antibody and the toxin but also between antibody and antibody, and toxin and toxin, and moreover, they effect the formation of intra-molecule bonds in the antibody and in the toxin molecule, thus causing the formation of undesirable products and decrease or loss of the antitumor activity.

SUMMARY OF THE INVENTION

The present inventors have achieved this invention as a result of their earnest research work to overcome such disadvantages as found in the prior art by developing an antitumor substance which displays strong cytotoxicity against, for example mice tumor cells selectively.

The present invention relates to an antitumor protein hybrid, composed of a moiety which is substantially the fragment Fab of an antitumor immunoglobulin and a moiety which is substantially the fragment A of a diphtheria toxin, which is expressed by the following formula (I):

$$\text{Fab}(-S_1-(X)_n-S_2-FA)_m \qquad (I)$$

(where Fab indicates a moiety which is substantially the fragment Fab of an antitumor immunoglobulin; FA indicates a moiety which is substantially the fragment A of a diphtheria toxin; X indicates a divalent organic radical; $S_1$ and $S_2$ are both sulfur atoms, $S_1$ indicating a sulfur atom arising from the —S—S— bond in an immunoglobulin and $S_2$ a sulfur atom arising from the —S—S— bond in a diphtheria toxin; n stands for 0 or 1 and m stands for an integer of 1 to 5), and a process for preparing said antitumor protein hybrid, which process comprises binding the sulfur atom in said fragment Fab with the sulfur atom in said fragment A directly or indirectly.

DESCRIPTION OF THE PREFERRED EMBODIMENTS

What is called antitumor immunoglobulin in the present invention is a protein (immunoglobulin) which has an antibody activity (ability to recognize tumor antigen and couple thereto) prepared from, for instance, the serum of a patient with cancer or serum obtained from such animals as monkeys, horses, cows, goats, sheep, rabbits, etc. which are hyperimmunized with cancer cells or cancer antigen according to a publiciy known method such as the Cohn ethanol fractionation method, ammonium sulfate fractionation method, ion-exchange chromatography, etc. Or it is a protein having an antibody activity of high selectivity to cancer antigen obtained from a culture fluid of hybridomas or from a serum or ascites of animals inoculated with hybridomas which are prepared by fusing antibody producing lymphocyte obtained by immunizing animals with cancer cells or cancer antigen, for instance, with myeloma (See, for instance, H. Koprowski, et al., Proc. Natl. Acad. Sci. U.S.A., Vol. 75, No. 7. pp 3405-3409, 1978; K. E. Hellström, et al., Proc. Natl. Acad. Sci. U.S.A., Vol. 76, No. 6, pp 2927-2931, 1979; R. H. Kennett, et al., Science, Vol. 203, pp 1120-1121, 1979.) A protein, which has antibody activity, prepared by isolating an antitumor antibody from a tumor tissue with a denaturant such as surface active agent, etc., followed by the same processing procedure as mentioned above, is also included under the antitumor immunoglobulin according to the present invention.

Figure 1A:
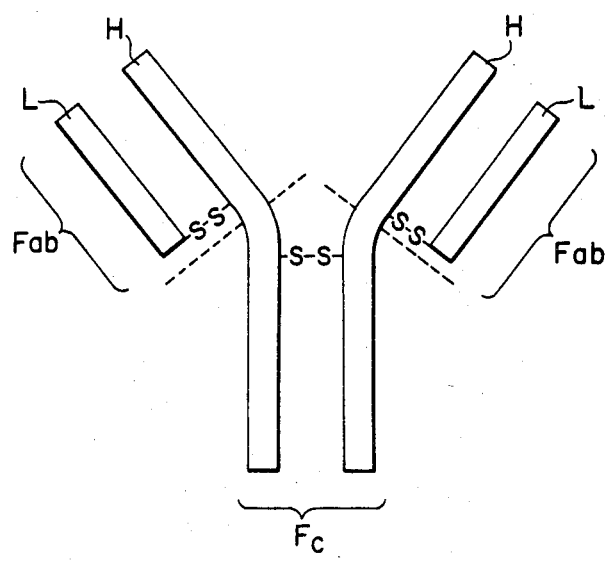
In FIG. 1, (a) is a pictorial drawing of a type specimen to show a basic structure of the immunoglobulin and (b) is a pictorial drawing of a type specimen to show a structure of IgG1 of human immunoglobulin.
Figure 1B:
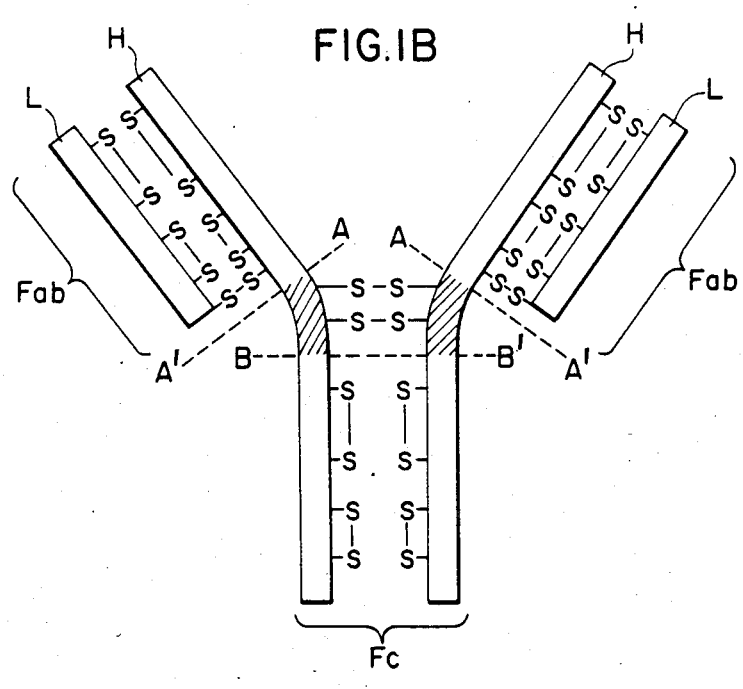

It is known that there are five major classes of immunoglobulins, IgG, IgA, IgM, IgD and IgE, and that their basic structure comprises, as shown by a pictorial drawing of a type specimen in FIG. 1, (a), two L chains which are indicated by L in the figure and two H chains indicated likewise by H, all chains being found with at least three disulfide bonds (—S—S— bonds). To explain the basic structure of the immunoglobulin shown in FIG. 1, (a), it consists of two Fab parts which are shown by Fab in the figure and an Fc part shown by Fc; Fab parts have antibody activity, or more particularly the ability to selectively couple to the antigen; the Fc part has the ability to couple to complements or Fc receptors on the cell membrane.

The moiety substantially comprising the fragment Fab which is one moiety of the antitumor protein hybrid of the present invention corresponds to the moiety comprising the fragment having an antibody activity arising from said Fab part of the immunoglobulin. For instance, it is known that IgG1, which is typical of human immunoglobulins, has a structure shown by a pictorial drawing of a type specimen of FIG. 1, (b) and, when subjected to papain digestion in the presence of cystine, this immunoglobulin is cleaved on the broken lines A-A' into two Fab fragments and one Fc fragment as shown in FIG. 1, (b), and the Fab fragments thus obtained can be used as fragment Fab in the present invention. When said IgG1 is treated with pepsin, it is cleaved on the broken line B-B' as shown in FIG. 1, (b), to produce a dimer, (F(ab')$_2$), of Fab'·part consisting of the Fab part and the hinge part which is shaded with oblique lines in the figure. Two Fab' fragments can also be obtained by cleaving the disulfide bond in the hinge part reductively, for instance, with the use of a thiol reagent or by cleaving it by means of sulfonation with sulfite ions. Since this Fab' fragment has an antibody activity like the Fab fragment (though it does not have the ability to couple to complements), it can be used as fragment Fab of the present invention. In the present invention, so long as the fragment Fab has an antibody activity, said Fab fragment or Fab' fragment may be the one chemically modified.

Thus obtained fragment Fab is used for the preparation of antitumor protein hybrid according to the present invention just as it is so long as it has at least one thiol radical (—SH) and/or S-sulfo radical (—S—SO$_3^-$) in the fragment but in other cases it is used after it has been changed into a fragment having at least one thiol radical and/or S-sulfo radical by cleaving at least one of the disulfide bonds in the chains (in the H chains or the L chains) and the disulfide bonds between the chains (between the H chains and the L chains) according to publicly known methods. The number of thiol radicals and/or S-sulfo radicals in the fragment Fab should preferably be in the range of 1-5 (corresponding to m=1-5 in the formula (I)) and it is especially preferable to have the number of thiol radicals and/or S-sulfo radicals which are formed by cleaving the bonds between the chains within the range of 1-2 (corresponding to m=1-2 in the formula (I)).

Figure 2A:
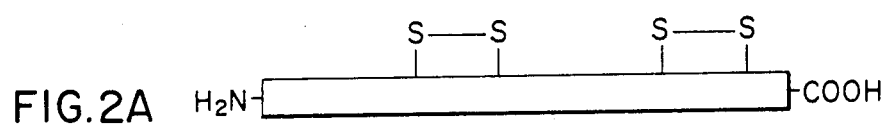
FIG. 2 is pictorial drawings of a type specimen of diphtheria toxin, wherein (a) shows a structure of intact toxin, (b) shows a structure of nicked toxin, and (c) shows structures of fragment A and fragment B.
Figure 2B:
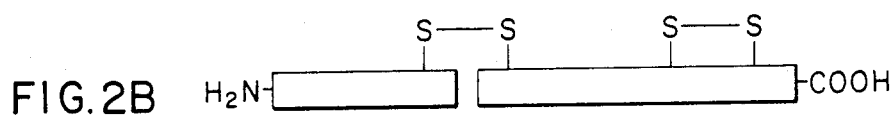
Figure 2C:
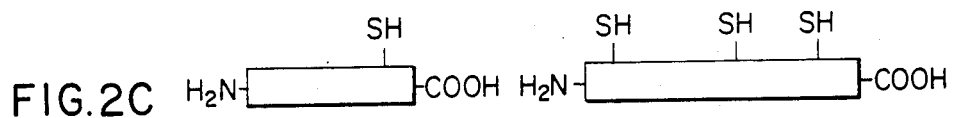

What is called diphtheria toxin in the present invention is a protein toxin produced by *Corynebacterium diphtheriae* or its mutant. For instance, a diphtheria toxin produced by *Corynebacterium diphtheriae* consists of a single polypeptide chain having molecular weight of about 62,000-63,000 and this is called an intact toxin. The intact toxin has two disulfide bonds (—S—S— bonds) in its molecule as shown in a pictorial drawing of a type specimen of FIG. 2, (a). When this intact toxin is treated under moderate conditions with such a proteolytic enzyme as trypsin, there occurs a separation at a specific point in the disulfide bond nearer to the amino-terminal to form a nicked toxin as shown in FIG. 2, (b). When this nicked toxin is treated with a reducing agent, it is divided into fragment A having a molecular weight of about 24,000 and fragment B having a molecular weight of about 38,000-39,000 as shown in FIG. 2, (c). The intact toxin has a very strong toxicity against animals; however, fragement A and fragment B themselves are both nontoxic. On the other hand, the intact toxin has no adnosine diphosphate (ADP)-ribose transferase activity on the elongation factor 2 (EF-2) defined below, while fragment A has transferase activity. And though fragment B has no transferase activity, it has the capability of coupling to a cell receptor which fragment A does not possess.

In the present invention, the moiety substantially comprising fragment A which forms one of the moieties of the antitumor protein hybrid means a moiety composed of a fragment of the diphtheria toxin which satisfies the aforementioned characteristics of fragment A, namely the following two characteristics:

(1) To have ADP-ribose transferase activity on EF-2.

(2) To have no capability of coupling to a cell receptor and no cytotoxicity by itself.

So long as the abovementioned two requirements are satisfied, nontoxic protein produced by mutant (which has one disulfide bond in the molecule) such as CRM 30 and CRM 45 produced, for instance, from Corynebacterium diphtheriae mutant such as $C_7$ ($\beta$30) and $C_7$ ($\beta$47) and the fragment obtained by treating them under moderate conditions with trypsin in the presence of such a reducing agent as thiol reagent are included in fragment A of the present invention.

Fragment A thus obtained is used for the preparation of the antitumor protein hybrid of the present invention just as it is without being subjected to any treatment when it has at least one thiol radical in the fragment or after its thiol radical is converted to an S-sulfo radical on treatment with sulfite ions. When it has one disulfide bond in the fragment, it is used after conversion into a fragment having at least one thiol radical and/or S-sulfo radical by cleaving the disulfide bond according to a publicly known method.

As for fragment A in the present invention, a fragment having one thiol radical or S-sulfo radical in the molecule is especially preferable.

Incidentally, the ADP-ribose transferase activity on EF-2 is defined as follows.

EF-2 is known as a protein elongation factor which is related to protein synthesis of cells and fragment A of the diphtheria toxin deactivates EF-2 by catalytically promoting the reaction mentioned below between EF-2 and nicotinamideadeninedinucleotide (NAD):

$$\text{EF-2}+\text{NAD}^+\rightarrow\text{(ADP ribose)-(EF-2)}+\text{nicotinamide}+\text{H}^+$$

The performance to promote this reaction is defined as ADP-ribose transferase activity on EF-2.

ADP-ribose transferase activity on EF-2 acts to interfere with protein synthesis and works as the entity of lethaltoxicity for animals; however, it is necessary for fragment A of the diphtheria toxin which has this ADP-ribose transferase activity on EF-2 to have fragment B which is capable of coupling to a cell receptor in order that fragment A enters into the cell and exerts its cytocidal effect: fragment A alone can not cause death in animals.

In the present invention, when fragment Fab of antitumor immunoglobulin having at least one thiol radical and/or S-sulfo radical in the fragment is reacted directly with fragment A of the diphtheria toxin having at least one thiol radical and/or S-sulfo radical in the fragment under the reaction conditions mentioned later, antitumor protein hybrids expressed by the undermentioned formula (I') which corresponds to the aforementioned formula (I) wherein n=0 are obtained.

$$\text{Fab}(\!-S_1-S_2-\text{FA})_m \qquad \text{(I')}$$

(where the definitions of Fab, FA, m, $S_1$ and $S_2$ are the same as those given in case of formula (I)). Of these, the one which has a structure expressed by the following formula (II) is especially preferable from the viewpoint of ease of preparation, separation and purification:

$$\text{Fab}(\!-S_1-S_2-\text{FA})_p \qquad \text{(II)}$$

(where the definitions of Fab, FA, $S_1$ and $S_2$ are the same as those given in case of formula (I): p indicates 1 or 2).

In the present invention, the divalent organic radical, which is expressed by X where n=1 in the aforementioned formula (I), means an organic radical arising from a cross-linking agent having in the molecule at least two functional groups capable of forming a sulfide bond (—S— bond) by reacting with a thiol radical (—SH). Such cross-linking agents involve, for instance, a bismaleimide compound which is expressed by the undermentioned formula (III), bishalocarbonyl compound which is expressed by the formula (IV), dihaloketone compound expressed by the formula (V), and halocarbonylmaleimide compound expressed by the formula (VI):

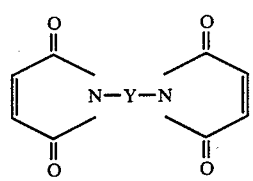

(III)

(where Y indicates a divalent organic radical).

$$X_1-CH_2-\underset{\underset{O}{\|}}{C}-Z-\underset{\underset{O}{\|}}{C}-CH_2-X_2 \qquad \text{(IV)}$$

(where Z indicates a divalent organic radical, $X_1$ and $X_2$ are the same or differ from each other indicating bromine or iodine).

$$X_1-CH_2COCH_2-X_2 \qquad \text{(V)}$$

(where $X_1$ and $X_2$ are the same or differ from each other indicating bromine or iodine).

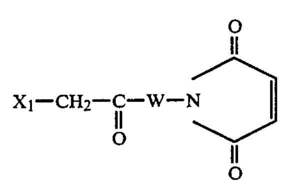

(VI)

(where W indicates a divalent organic radical and $X_1$ indicates bromine or iodine).

Specific examples of bismaleimide compound expressed by the abovementioned formula (III), are, for instance, N,N'-(1,3-phenylene)dimaleimide, N,N'-(1,4-phenylene)dimaleimide, 4,4'-bis(maleoylamino)azobenzene, and bis(N-maleimidomethyl)ether. Specific examples of bishalocarbonyl compound expressed by the formula (IV), are N,N'-alkylenebis(bromoacetamide) and N,N'-alkylenebis(iodoacetamide) (wherein the alkylene radical has 2–15 carbon atoms). Specific examples of dihaloketone compound expressed by the formula (V), are 1,3-dibromoacetone and 1,3-diiodoacetone. Specific examples of halocarbonylmaleimide compound, are N-(α-bromoacetoxymethyl)maleimide and N-(α-iodoacetoxymethyl)maleimide. And as for cross-linking agents having three functional groups, for instance, 1,2,4-tris(maleoylamino)benzene, 1,3,5-tris(maleoylamino)benzene may be mentioned.

The antitumor protein hybrid of the present invention can be prepared according to the methods given in the following.

(1) A method either to make a substantial fragment Fab which has at least one S-sulfo radical in the fragment react with a substantial fragment A which has at least one thiol radical in the fragment or to make a substantial fragment Fab which has at least one thiol radical in the fragment react with a substantial fragment A which has at least one S-sulfo radical in the fragment.

In these methods, it is preferable to use a ratio of 0.3 to 3 moles of fragment A to 1 mole of fragment Fab. The reaction can be conducted by mixing fragment Fab and fragment A in a buffer solution whose pH is in the range of 6 to 10 to make a total protein concentration of 0.5 to 100 mg/ml (more preferably 1 to 20 mg/ml) and leaving the mixture at 0° to 60° C. or dialyzing the reaction mixture against a buffer solution having the same pH value as the reaction mixture. The reaction time generally extends over a period of four hours to three days, depending upon the scale and conditions of the reaction. The separation of the hybrid thus composed of fragment Fab and fragment A from the reaction mixture and the purification can be carried out according to a usual procedure, for instance, of dialysis or column chromatography of molecular sieve effect.

The method mentioned above allows the reaction to proceed smoothly under very moderate conditions to offer a highly purified hybrid. The method also has the advantage of permitting the selective formation of hybrid composed of fragment Fab and fragment A (as compared to the formation of hybrid effected between fragments Fab themselves or between fragments A themselves coupled by the disulfide bond).

(2) A method for binding a substantial fragment Fab which has at least one thiol radical in the fragment and a substantial fragment A which has at least one thiol radical in the fragment with the use of any of the aforementioned cross-linking agents expressed by the formula (III), (IV), (V) or (VI).

in the above method, the reaction can be conducted by bringing the fragment Fab, cross-linking agent and fragment A into contact with each other simultaneously; however, it is preferable to carry out the preparation of the hybrid by making fragment A react with the reaction product obtained by first allowing fragment Fab to react with the cross-linking agent or by making fragment Fab react with the reaction product obtained by first allowing fragment A to react with the cross-linking agent. In the former case, it is preferable to use 0.8 to 6 moles of the cross-linking agent and fragment A respectively to 1 mole of fragment Fab. In the latter case, it is preferable to use 0.8 to 3 moles of the cross-linking agent and 0.2 to 3 moles of fragment Fab to 1 mole of fragment A. The reaction is started at 0° to 60° C. with stirring with the addition of the cross-linking agent dissolved in a small amount of solvent such as N,N-dimethylformamide, dimethyl sulfoxide, 1,2-dimethoxyethane, methanol, ethanol, acetone, etc. to a solution of fragment Fab or fragment A buffered at a pH of 6 to 10 (the protein concentration being preferably controlled to 0.5 to 100 mg/ml, or more preferably to 1 to 20 mg/ml). After the removal of the cross-linking agent left unreacted by means of dialysis or column chromatography of the molecular sieve effect, another fragment solution buffered at a pH of 6 to 10 (the preferable ranges of protein concentration being the same as mentioned above) is added to carry out the reaction at 0° to 60° C. The separation, and purification as well, of the thus obtained hybrid of fragment Fab and fragment A from the reaction mixture can be effected according to a usually adopted method such as column chromatography of the molecular sieve effect.

(3) A method in which fragment Fab of the antitumor immunoglobulin which has at least one thiol radical in the fragment and fragment A of the diphtheria toxin which has at least one thiol radical in the fragment are subjected to the oxidative reaction in the state of coexistence with each other to have them both bound by the disulfide bond. As for the oxidative reaction, any of the air oxidation method, method of oxidation using o-iodobenzoic acid and method in which oxidation is effected with o-phenanthroline and cupric sulfate may be adopted.

(4) A method in which either fragment Fab or fragment A is first made to react with Ellman's reagent 5,5'-dithiobis(2-nitrobenzoic acid)), 2,2'-dipyridyldisulfide, 4,4'-dipyridyldisulfide or tetrathionate and the reaction product thus obtained is then made to react with another of the above fragments.

In the present invention, (1) and (2) of the abovementioned methods are especially preferable.

The antitumor protein hybrid of the present invention consists of a moiety substantially comprising fragment A which demonstrates toxicity against tumor cells and a moiety substantially comprising fragment Fab which specifically recognizes a tumor cell and works as a carrier to guide said fragment A to the tumor cell and to take fragment A into the cell as well and this hybrid has excellent characteristics mentioned below.

(1) Since the hybrid of the present invention does not contain the Fc part of the immunoglobulin, nonspecific binding to Fc receptors on the cell membrane with the Fc part is avoided and this fact allows the antibody activity or performance of the fragment Fab to selectively couple to the antibody to be demonstrated predominantly.

(2) It is known that, when a xenogeneic immunoglobulin is used, it is the Fc part that has the strongest antigenicity. In case of the hybrid according to the present invention, since it does not contain the Fc part of the immunoglobulin, the antigenicity of the xenogeneic immunoglobulin is reduced remarkably.

(3) It is known that, in case of diphtheria toxin, it is the fragment B that has the ability to couple to the receptor of cells (normal cells and tumor cells) and that the fragment A can be taken into the cell by means of the coupling of the fragment B to the cell membrane to demonstrate cytotoxicity. However, since the hybrid of the present invention does not contain the fragment B, the hybrid of the present invention does not demonstrate cytotoxicity to normal cells. Furthermore, since it does not contain the fragment B, the antigenicity of the diphtheria toxin is also reduced.

(4) The hybrid of the present invention has a moiety substantially comprising the fragment Fab obtained from the antitumor immunoglobulin and this moiety specifically recognizes a tumor cell and makes the tumor cell take in specifically the moiety substantially comprising the fragment A of the diphtheria toxin. The fragment A thus taken in demonstrates a remarkable cytotoxicity to the tumor cell.

The present invention is described in detail by the following examples. The measurement of the ADP-ribose transferase activity on EF-2 and the measurement of the concentration of fragment Fab' according to the single radial immunodiffusion referred to in the examples were made according to the method mentioned below.

(1) ADP-ribose transferase activity on EF-2

EF-2 was obtained from the homogenate of the rat liver and was used after partially refined by centrifugation (12,000×g, supernatant fraction after twenty minutes), ammonium sulfate fractionation (supernatant of 40% saturation and precipitate of 60% saturation) and DEAE Sephadex column chromatography (equilibrated with 10 mM (m mole/l) Tris.HCl-50 mM potassium chloride, and 1 mM aqueous solution of 2-mercaptoethanol (pH 7.6)).

80 p mole of EF-2, 45 p mole of $^{14}C$ labeled $MAD^+$ (6550 cpm) and 30 μl of the test specimen (prepared by diluting each fraction from column chromatography 10 to 100 times) were added to 0.1 ml of aqueous solution (pH 7.6) of 0.1M Tris.HCl-20 mM dithiothreitol—2 mM ethylenediaminetetraacetic acid and made to react at 37° C. for ten minutes. Immediately after the reaction was over, 0.5 ml of 5% trichloroacetic acid was added while cooling with an ice-bath and the precipitated substance (insoluble in acid) was collected on a 0.45μ Millipore filter. The radioactivity of thus obtained precipitate (insoluble in acid) was measured with a liquid scintillation counter to determine the function of the test specimen to promote the undermentioned reaction or ADP-ribose transferase activity on EF-2 (the strength of the radioactivity of the precipitate is proportional to the amount of deactivated EF-2) by means of a calibration curve prepared beforehand:

$$EF-2 + NAD^+ \longrightarrow (ADP\ ribose) - \underset{\text{Insoluble in acid}}{\Vert}$$

$$(EF-2) + nicotinamide + H^+$$

(2) Concentration of fragment Fab' (single radial immunodiffusion)

Dithiothreitol was added to 50 μl of the respective fractions obtained from Sephadex column chromatography in such an amount as to make a concentration of 20 mM, the reductive reaction was carried on at 37° C. for 30 minutes (to have the disulfide bond cleaved into two thiol radicals) and the reaction was conducted at 20° C. for 30 minutes after iodoacetamide was added in such an amount as to make a concentration of 50 mM (the thiol radicals were blocked). The test specimen solution thus pretreated was placed in a well on the agar which contained goat anti-rabbit IgG serum and was left standing for two days. The diameter of the ring of precipitate formed as a result of the antigen-antibody reaction was measured to determine the concentration of the fragment Fab' by means of a calibration curve prepared beforehand. However, in Examples 3 to 9, no pretreatment was made and 50 μl of the respective fractions were used as they were as test specimens (in this case, it is hard to obtain precise values quantitatively but qualitative data can be obtained satisfactorily).

EXAMPLE 1

(a) Preparation of fragment Fab' of antitumor immunoglobulin

Mouse leukemia L 1210 cells transplanted successively on DBA/2Cr mice were taken out of the ascites of a DBA/2Cr mouse. An emulsion prepared from about $10^6$ of those cells and Freund's complete adjuvant (immuno adjuvant) was intravenously injected into a rabbit. After that $10^6$ L 1210 cells, together with the adjuvant, were subcutaneously injected three times at one-week intervals, and the rabbits were bled seven days and ten days after the day of final administration. The blood thus obtained was mixed and serum was separated from the mixed blood and was inactivated at 56° C. for 30 minutes. 200 ml of saturated aqueous ammonium sulfate solution was added to 200 ml of thus obtained serum (anti L 1210 serum) at 4° C. and the precipitate (anti L 1210 immunoglobulin) was separated by means of centrifugation. The precipitate thus obtained was dissolved in 50 ml of 0.01M phosphate buffer solution (pH 7.6) and was sufficiently purified by dialysis against the same buffer solution to obtain a solubion of anti-L 1210 immunoglobulin. The solution was put to DEAE cellulose column chromatography (column size 3 cm×94 cm) equilibrated with the same phosphate acid buffer solution to obtain a solution containing IgG as an unadsorbed fraction. 24 mg of pepsin was added to 40 ml of anti-L 1210 IgG solution (30 mg/ml) obtained by dialyzing thus obtained solution against 0.1M acetate buffer (pH 4.5). The pepsin digestion was carried out at 37° C. for about 18 hours and the digestion product was put to Sephadex G200 column chromatography (column size 3.5 cm×140 cm) over saline to take out protein eluted at a molecular weight of about 100,000. It was confirmed that this was purely a dimer of fragment Fab' by means of electrophoresis with sodium dodecyl sulfate. 0.04 ml of 100 mM 2-mercaptoethanol was added to 2.0 ml of a solution (7.3 mg/ml) of the dimer of fragment Fab' obtained by dialyzing isotonic sodium chloride solution of the dimer of fragment Fab' ($F(ab')_2$) thus obtained against an aqueous solution (pH 8.3) of 0.01M Tris.HCl-0.14M sodium chloride-2 mM ethylenediaminetetraacetic acid. The reduction with 2-mercaptoethanol was carried out at 37° C. for one hour and then substances of low molecular weight were removed by dialyzing against saline to obtain a fragment Fab' solution of anti-L 1210 immunoglobulin having a thiol radical (or having one thiol radical arising from one disulfide bond at the hinge part).

(b) Preparation of fragment A of diphtheria toxin 0.15 ml of a trypsin solution having a concentration of 0.1 mg/ml was added to 18.5 ml of an aqueous solution (pH 8.3) of 0.05M Tris.HCl-2 mM ethylenediaminetetraacetic acid containing 210 mg of diphtheria toxin, and the digestion was carried out at 25° C. for 50 minutes. After that 0.3 ml of a soybean trypsin inhibitor solution having a concentration of 0.5 mg/ml was added thereto to stop the reaction. Urea (final concentration 6M), sodium sulfate (final concentration 0.168M) and sodium tetrathionate (final concentration 0.042M) were added to the obtained digestion product and the mixture was subjected to S-sulfonating decomposition at 37° C. for two hours. The resulting reaction solution was subjected to Sephadex G 150 column chromatography (column size 3.5 cm×112 cm) over a buffer solution (pH 5.3) of 6M urea-0.03M acetic acid and only the fractions of fragment A which came out later were taken. These fractions were dialyzed against distilled water to give a pure fragment A solution (having one S-sulfo radical).

(c) Preparation of antitumor protein hybrid 2.5 ml of an aqueous solution containing 7.3 mg of fragment Fab' (having one thiol radical) of anti-L 1210 immunoglobulin IgG obtained according to the aforementioned (a) and 4.0 mg of fragment A (having one S-sulfo radical) of diphtheria toxin obtained according to the aforementioned (b) was prepared. This solution was dialyzed at 4° C. for three days against 1 l of aqueous solution (pH 9.15) of 0.05M glycine buffer-0.10M sodium chloride-2 mM ethylenediaminetetraacetic acid to effect the reaction to couple the fragment Fab' and the fragment A. The obtained product was subjected to Sephadex G150 column chromatography (column size 1.6 cm×93 cm) on an aqueous solution (pH 7.0) of 5 mM phosphate buffer—0.154M sodium chloride to give 60 fractions of 2.1 ml each. The absorbance at 280 μm was measured for each fraction to know the concentration of protein and the obtained result is shown by a solid line to indicate the pattern of protein elution in FIG. 3. As clearly shown in FIG. 3, there were four peaks in the pattern of protein elution and they were named peak 1, peak 2, peak 3, peak 4 in order of increasing molecular weight.

Figure 3:
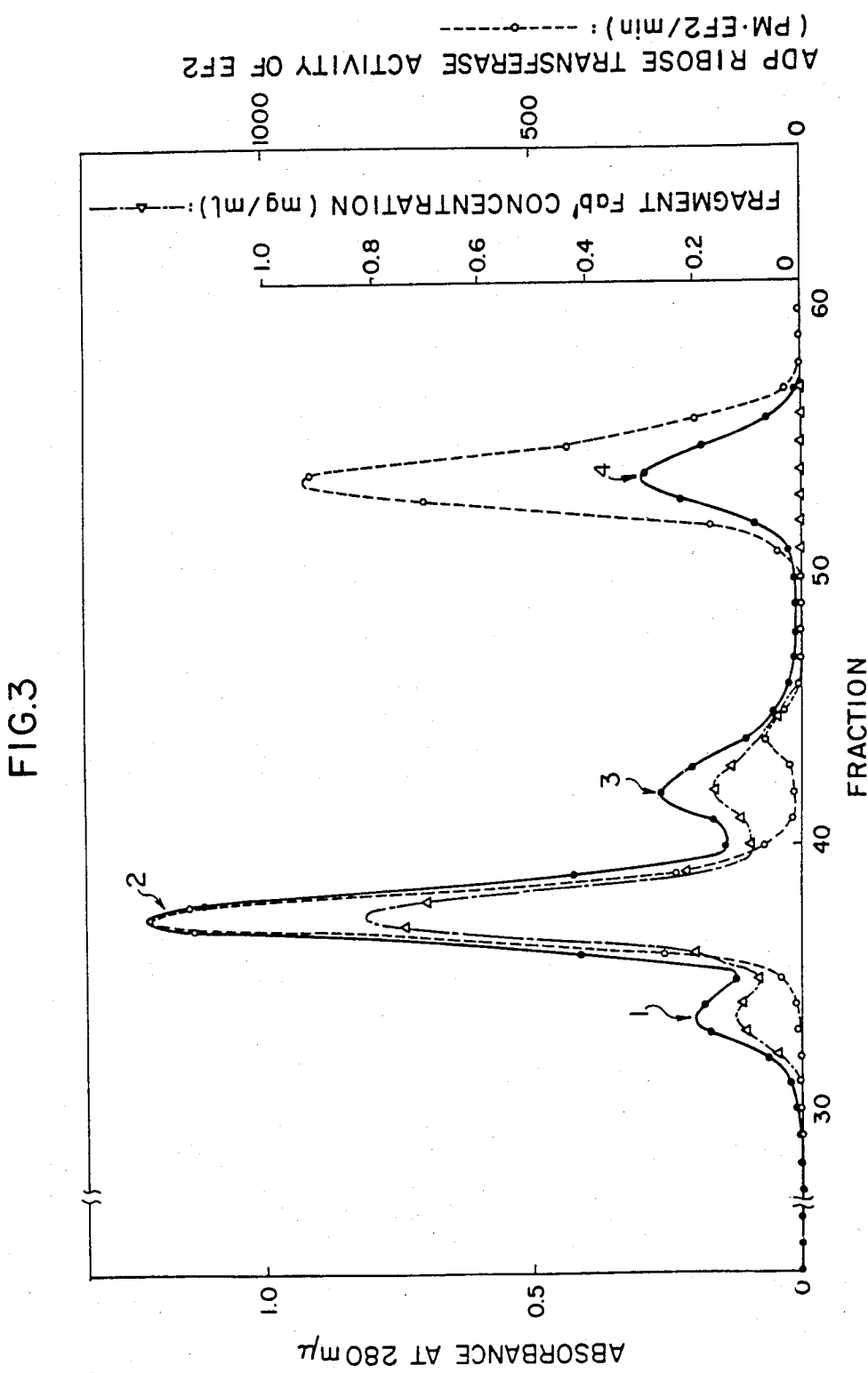
FIG. 3 shows the elution pattern (—•—) of a reaction product of fragment Fab' of anti L1210 immunoglobulin IgG and fragment A of diphtheria toxin by column chromatography on Sephadex G 150 superfine and the relationship of the elution pattern vs. ADP ribose transferase activity of EF-2 (- - - o - - -), and concentration of fragment Fab' (—•—Δ—o—).

The ADP-ribose transferase activity on EF-2 of the fractions corresponding to the respective peaks were measured and the results are shown by a broken line in FIG. 3. The measurement of the antigen-antibody reaction (radial immunodiffusion) with goat anti-rabbit IgG of the fractions corresponding to the respective peaks was made to know the concentration of fragment Fab' contained in fractions corresponding to the respective peaks and the results are shown by a dotted-broken line in FIG. 3.

FIG. 3 leads to the following assumption. The protein (having the largest molecular weight) corresponding to peak 1 has no ADP-ribose transferase activity on EF-2 and contains only fragment Fab', so it is assumed to be a dimer of fragment Fab'. The protein corresponding to peak 2 has transferase activity and also contains fragment Fab' leading to an assumption that it is a reaction product of fragment Fab' and fragment A. The protein corresponding to peak 3 is a mixture of protein comprising fragment Fab' only and protein which does not contain fragment Fab' but has transferase activity, therefore this protein is assumed to be a mixture of fragment Fab' and the dimer of fragment A. The protein corresponding to peak 4 (having the smallest molecular weight) does not contain fragment Fab' but has transferase activity, therefore it is assumed to be fragment A.

Figure 4:
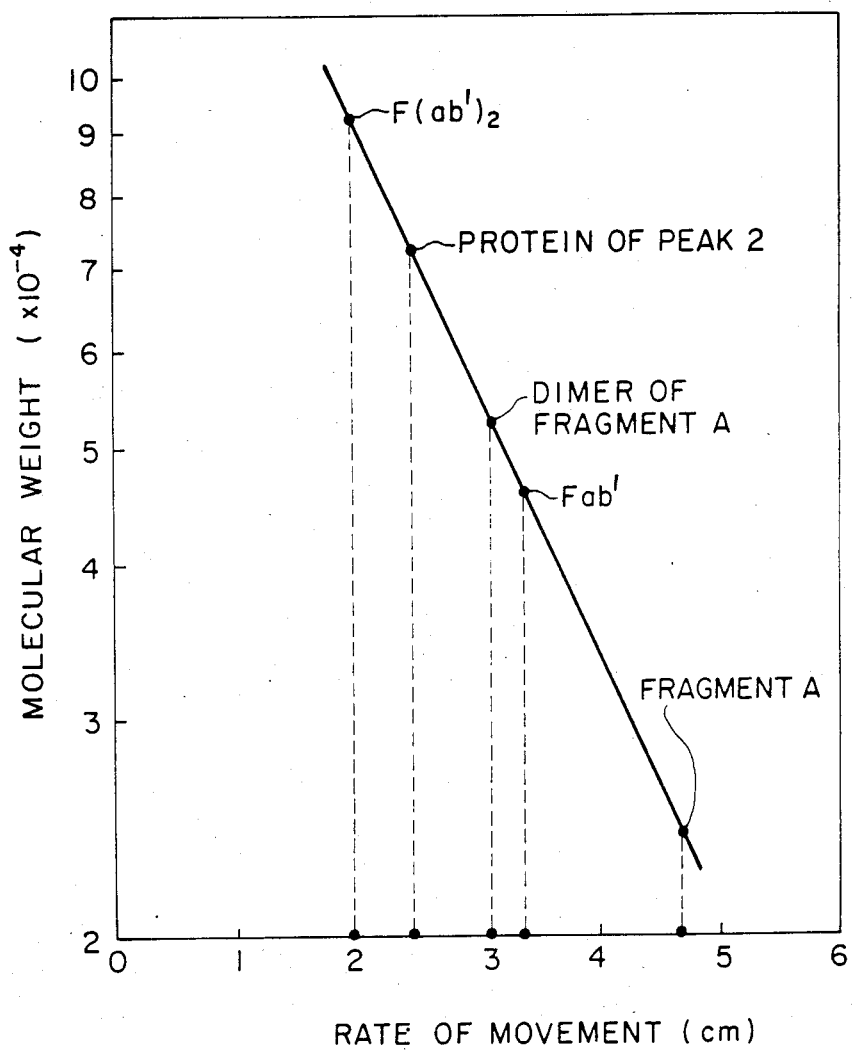
FIG. 4 is an explanatory drawing to show the relationship between the rate of movement in electrophoresis using sodium dodecyl sulfate.

The above assumption was supported by the results of measurement of rate of movement obtained in sodium dodecyl sulfate electrophoresis conducted on the dimer of fragment Fab', (F(ab')2), protein corresponding to peak 2 (the 37th or 38th fraction), the dimer of fragment A, fragment Fab', and fragment A. In FIG. 4, the arrangement of F(ab')2, protein of peak 2, the dimer of fragment A, Fab', and fragment A is in the order of decreasing rate of movement or in the order of increasing molecular weight, and this arrangement corresponds to the arrangement of peaks 1, 2, 3 and 4 in the order of increasing molecular weight shown in FIG. 3.

In FIG. 4, it can be seen that the protein corresponding to peak 2 has a molecular weight of about $7\times10^4$ which matches well with the molecular weight of about 70,000 obtained as the sum of the molecular weight of about 46,000 of fragment Fab' and the molecular weight of about 24,000 of fragment A. It has therefore been confirmed that the protein corresponding to peak 2 is the protein hybrid, which is the object of the present invention, comprising fragment Fab' and fragment A linked by the disulfide bond.

(d) Measurement of cytotoxicity of antitumor protein hybrid

Part 1: An aqueous solution was prepared by mixing the 37th and the 38th fractions corresponding to the aforementioned peak 2 in such a way as to contain the protein hybrid of the present invention at the concentration of 0.84 mg/ml. The cytotoxicity of the protein hybrid of the present invention against mouse leukemia cells L 1210 was measured with the use of this solution.

A culture fluid was prepared by suspending $5\times10^4$ of L 1210 cells in the medium of RPMI 1640 (containing 10% fetal calf serum and 20 μM 2-mercaptoethanol and also containing kanamycin sulfate at a concentration of 100 μg/ml). The same culture fluid was prepared in five separate lots and the mixture was incubated at 37° C. in an atmosphere of 5% $CO_2$ for 42 hours with nothing added to one lot, diphtheria toxin added to another lot, and the protein hybrid of the present invention prepared according to the preceding (c) added to the remaining three lots.

After the culture was over, the cells of the respective lots of culture fluid were subjected to Trypan Blue dyeing to dye the dead cells to determine the number of viable cells under the microscope. The result is shown in Table 1.

TABLE 1

| Cytotoxicity of antitumor protein hybrid against L 1210 | |
|---|---|
| | Number of viable L 1210 cells after 42-hour incubation (%) |
| Not treated | $8 \times 10^5$ (100) |
| Diphtheria toxin, 40 μg/ml | $5 \times 10^5$ (63) |
| Antitumor protein hybrid, | |
| 0.5 μg/ml | $0.5 \times 10^5$ (6.3) |
| 5 μg/ml | $0.03 \times 10^5$ (0.4) |
| 50 μg/ml | $<0.01 \times 10^5$ (<0.1) |

Table 1 has made it clear that the initial $5\times10^4$ cells increased remarkably to 5 to $8\times10^5$ when to the culture fluid was added nothing or diphtheria toxin, while the number of viable cells was remarkably reduced when to the culture fluid was added the antitumor protein hybrid of the present invention (no measurement is possible for the cells less than 1000). Incidentally, it is known that mouse cells are not susceptible to diphtheria toxin.

Part 2: Cytotoxicity of the respective samples were examined in the same way as Part 1 of Measurement of cytotoxicity of antitumor protein hybrid mentioned above by cultivating $2\times10^4$ of mouse leukemia L-1210 cells for 48 hours in the medium RPMI 1640 comprising 10% fetal calf serum, 20 mM 2-mercaptoethanol and kanamycin sulfate at a concentration of 100 μg/ml with the addition of various samples shown in Table 2. For comparison's sake, L 1210 cells were cultivated in a system to which no samples were added (untreated) and the number of viable cells were examined after 42 hours. The results are shown in Table 2.

TABLE 2

| | Concentration μg/ml | The number of viable L 1210 after 42-hour incubation (%) |
| --- | --- | --- |
| Untreated | — | $3.07 \times 10^5$ (100) |
| Diphtheria toxin | 40 | $1.71 \times 10^5$ (56) |
| Fab' | 34 | $1.07 \times 10^5$ (35) |
| Fragment A | 18 | $1.50 \times 10^5$ (49) |
| Fab' + fragment A (molar ratio 1:1) | 51 | $1.43 \times 10^5$ (47) |
| | 5.6 | $2.00 \times 10^5$ (65) |
| Antitumor protein hybrid | 51 | $<0.01 \times 10^5$ (<0.3) |
| Antitumor protein hybrid | 5.1 | $<0.01 \times 10^5$ (<0.3) |
| Antitumor protein hybrid | 0.56 | $0.17 \times 10^5$ (5.5) |
| Antitumor protein | 0.056 | $1.60 \times 10^5$ (52) |

In the case where the antitumor protein hybrid of the present invention was added, even at such a low concentration as 0.56 μg/ml, the number of viable cells at the time of measurement was $1.7 \times 10^4$ (5.5% as compared with the control), and when the concentration of the added hybrid was 5.1 μg/ml, the number of viable cells was less than $10^3$ (counting is impossible when the number is less than $10^3$) (less than 0.3% as compared with the control). As Table 2 indicates clearly, such strong cytotoxicity was hardly observed with either fragment Fab' or fragment A. Also the mixture of equimolar solutions of fragment Fab' and of fragment A scarcely had an influence on the number of viable cells when compared with the control. This fact shows that the cytotoxicity of the antitumor protein hybrid does not arise from the mixed effect of fragment Fab' and fragment A.

Part 3: Three DBA/2 Cr mice per group were inoculated intraperitoneally with $1 \times 10^4$ L 1210 cells. On the following day, a prescribed dose of the antitumor protein hybrid of the present invention prepared according to the foregoing (c) was administered intraperitoneally to examine its effect on the prolongation of life-span. A control group of mice to which no antitumor protein hybrid was administered were also used. The results are shown in Table 3.

TABLE 3

| Dosage, μg/mouse | Period of survival (%) |
| --- | --- |
| 30 | 142 |
| 6 | 138 |
| 1.2 | 125 |
| Control (not administered)* | 100 |

*All the mice of the control group died in 8 days.

It it clearly shown in Table 3 that the mice, when administered with 1.2, 6, and 30 μg/mouse of the antitumor protein hybrid, had a period of survival of 125, 138, and 142%, respectively, as compared with the control group, which fact confirms an appreciable effect of prolonging life.

Since anti-L 1210 immunoglobulin, which was used in the aforementioned (c) Preparation of antitumor protein hybrid, did not undergo the process of absorption with the mouse normal tissue (a process to remove the antibody which recognizes the normal cells of a mouse), it contains an antibody which recognizes the normal cells of a mouse. Therefore, the toxicity exercised an influence also on the host mice and the mice had the period of survival extending only to 142% even though they were administered with the antitumor protein hybrid. It is clear that, if undergone the process of absorption mentioned above were undergone, the antitumor protein hybrid of the present invention would have an increased selective toxicity against tumor cells to show a greater remedial effect. If anti-L 1210 antibody is subjected to the adsorption process with tumor cells or tumor antigen, the content of tumor-specific antibody can be increased; however, since this process was not effected in this example, it is assumed that the content of tumor-specific antibody in the immunoglobulin obtained in said (a) was less than 1%. Accordingly, it is obvious that when the immunoglobulin having a high content of tumor-specific antibody is obtained according to said adsorption process and is used in the preparation of the antitumor protein hybrid, a greater remedial effect can be obtained with a smaller dosage.

EXAMPLE 2

(a) Preparation of fragment Fab' of antitumor immunoglobulin 21 mg of sodium sulfite and 13 mg of sodium tetrathionate were added to 3 ml of a saline solution containing 29 mg of the dimer of fragment Fab' of rabbit antibody (immunoglobulin IgG) against mouse leukemia L 1210 prepared according to Example 1, (a), and after the mixture was subjected to S-sulfonative cleavage at 37° C. for one hour to obtain fragment Fab' having a S-sulfo radical, the reagents were removed by dialysis.

(b) Preparation of fragment A of diphtheria toxin 0.05 ml of 0.5M aqueous solution of 2-mercaptoethanol was added to 1 ml of a solution of fragment A (4.8 mg/ml) obtained by dialyzing the solution of fragment A having one S-sulfo radical of diphtheria toxin prepared according to Example I, (b) against an aqueous solution (pH 8.3) of 0.01M Tris.HCl-0.14M sodium chloride—2 mM ethylenediaminetetraacetic acid, and the mixture was reduced at 37° C. for one hour. After that, 2-mercaptoethanol was removed by means of dialysis to obtain fragment A having one thiol radical.

(c) Preparation of antitumor protein hybrid 2 ml of an aqueous solution containing 5.8 mg of fragment Fab' prepared in the aforementioned (a) and 3.2 mg of fragment A prepared in the preceding (b) was prepared. This solution was dialyzed at 4° C. for three days against 1 l of an aqueous solution (pH 9.15) of 0.05M glycine buffer—0.10M sodium chloride—2 mM ethylenediaminetetraacetate acid to carry out the reaction to link both fragments. The reaction was followed by the same procedures as taken in Example 1 to give the protein hybrid, which is the object of the present invention, having fragment Fab' and fragment A linked with a disulfide bond.

EXAMPLE 3

(a) Preparation of antitumor protein hybrid 0.05 ml of 20 mM solution of o-phenylenedimaleimide (PDM) in N,N-dimethylformamide was added to 1 ml of an aqueous solution (pH 5.5) of 5 mM acetate buffer—0.14M sodium chloride—1 mM ethylenediaminetetraacetic acid containing 36.8 mg of fragment Fab' of anti-L 1210 immunoglobulin having one thiol radical obtained according to Example 1, (a), and the mixture was allowed to react at 30° C. for 30 minutes. The reaction mixture was subjected to gel-filtration on Sephadex G25 (column size 0.7 cm×35 cm) with 5 mM acetic acid buffer—0.14M sodium chloride—1 mM ethylenediaminetetraacetic acid (pH 5.5) to remove excessive reagents.

1.0 ml of an aqueous solution of fragment A (2.15 mg/ml) of diphtheria toxin having one thiol radical prepared according to Example 2, (b) and 0.2 ml of 0.3M sodium phosphate buffer (pH 6.5) were added to 1.04 ml of solution of fragment Fab' having the PDM residue (4.29 mg/ml) of anti-L 1210 immunoglobulin thus obtained, and the mixture was allowed to react at 4° C. overnight. Then the reaction mixture was subjected to Sephadex G150 superfine column chromatography (column size 1.6 cm×93 cm) with an 0.9% aqueous solution of sodium chloride to obtain a solution containing 4.4 mg of the antitumor protein hybrid by collecting the 38th to 42nd fractions.

Figure 5:
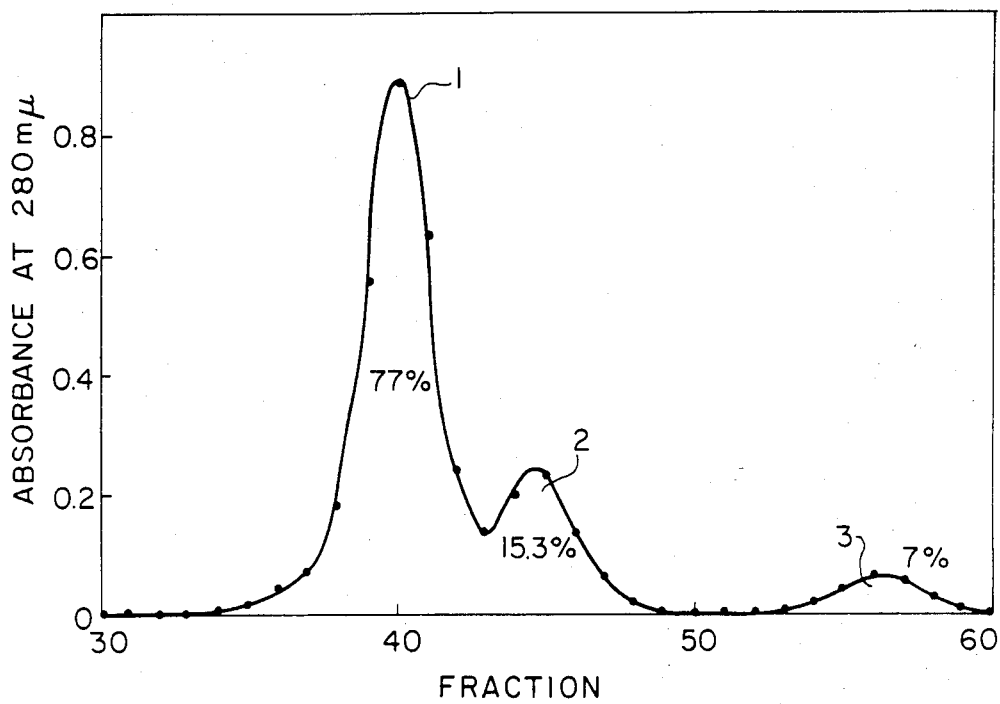
FIG. 5 is a figure to show the elution pattern by Sephadex G150 superfine column chromatography of the reaction product of fragment Fab' having the PDM residue of anti L1210 immunoglobulin IgG and fragment A of diphtheria toxin.
Figure 6:
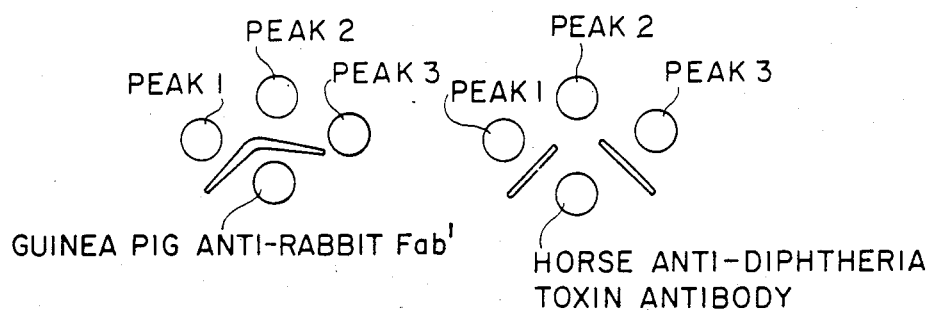
FIG. 6 is a figure to show the result of the analysis of the protein contained at the peaks 1,2, and 3 indicated in the elution pattern of FIG. 5 conducted according to the Ouchterlony method using guinea pig anti-rabbit Fab' antibody and horse anti-diphtheria toxin antibody.

It was confirmed according to the following method that what was contained in those fractions was the object substance. In order to know the protein concentration of the respective fractions obtained by said column chromatography, their absorbance was measured at 280 mµ. The resulting elution pattern of protein had three peaks 1, 2 and 3 as shown in FIG. 5. The proteins at those peaks were subjected to analysis according to the Ouchterlony method using guinea pig anti-rabbit Fab' antibody and horse anti-diphtheria toxin antibody and the results as shown in FIG. 6 were obtained. The proteins at peaks 1 and 2 formed a precipitate line with anti-rabbit Fab' antibody and those at peaks 1 and 3 with anti-diphetheria toxin antibody. Therefore, it is clear that peak 1 contains Fab' and fragment A of diphtheria toxin as well. Also it is known from the point of elution that the protein at peak 1 has a molecular weight of about 70,000, which corresponds to the total of molecular weight of fragment Fab' (46,000) and molecular weight of fragment A of diphtheria toxin (24,000). It may be concluded from the above results that the protein at peak 1 is the antitumor hybrid, comprising 1 molecule of fragment Fab' and 1 molecule of fragment A of diphtheria toxin bonded by PDM, which is the very object of the present invention. Incidentally, those proteins at peaks 2 and 3 are respectively fragment Fab' and fragment A of diphtheria toxin remaining not reacted, either modified or not modified by PDM.

(b) Measurement of cytotoxicity of antitumor protein hybrid

Mouse leukemia L 1210 cells ($3\times10^4$) were cultivated in an atmosphere of 5% carbon dioxide at 37° C. for 1, 2, 3, and 4 days respectively in 1-ml RPMI media each containing 10% fetal calf serum and 20 µM 2-mercaptoethanol, also containing kanamycin sulfate at the concentration of 100 µg/ml and the added antitumor protein hybrid prepared in the preceding (a) at the final concentration of 30, 6, and 1.2 µg/ml, respectively. For comparison's sake, L 1210 cells were cultivated in a medium with fragment Fab' and fragment A of diphtheria toxin added at a concentration of 20 µg/ml and 10 µg/ml respectively (at a molar ratio of 1:1) in the place of the antitumor protein hybrid. As for the control, L 1210 cells were cultivated in the system to which none of the antitumor protein hybrid, fragment Fab', and fragment A of diphtheria toxin was added. After the cultivation was over, uniform suspensions of cells were prepared with the use of a pipette, dyed with 0.3% Trypan Blue-phosphate buffered saline and the number of viable cells was counted under the microscope. The results are shown in FIG. 7.

Figure 7:
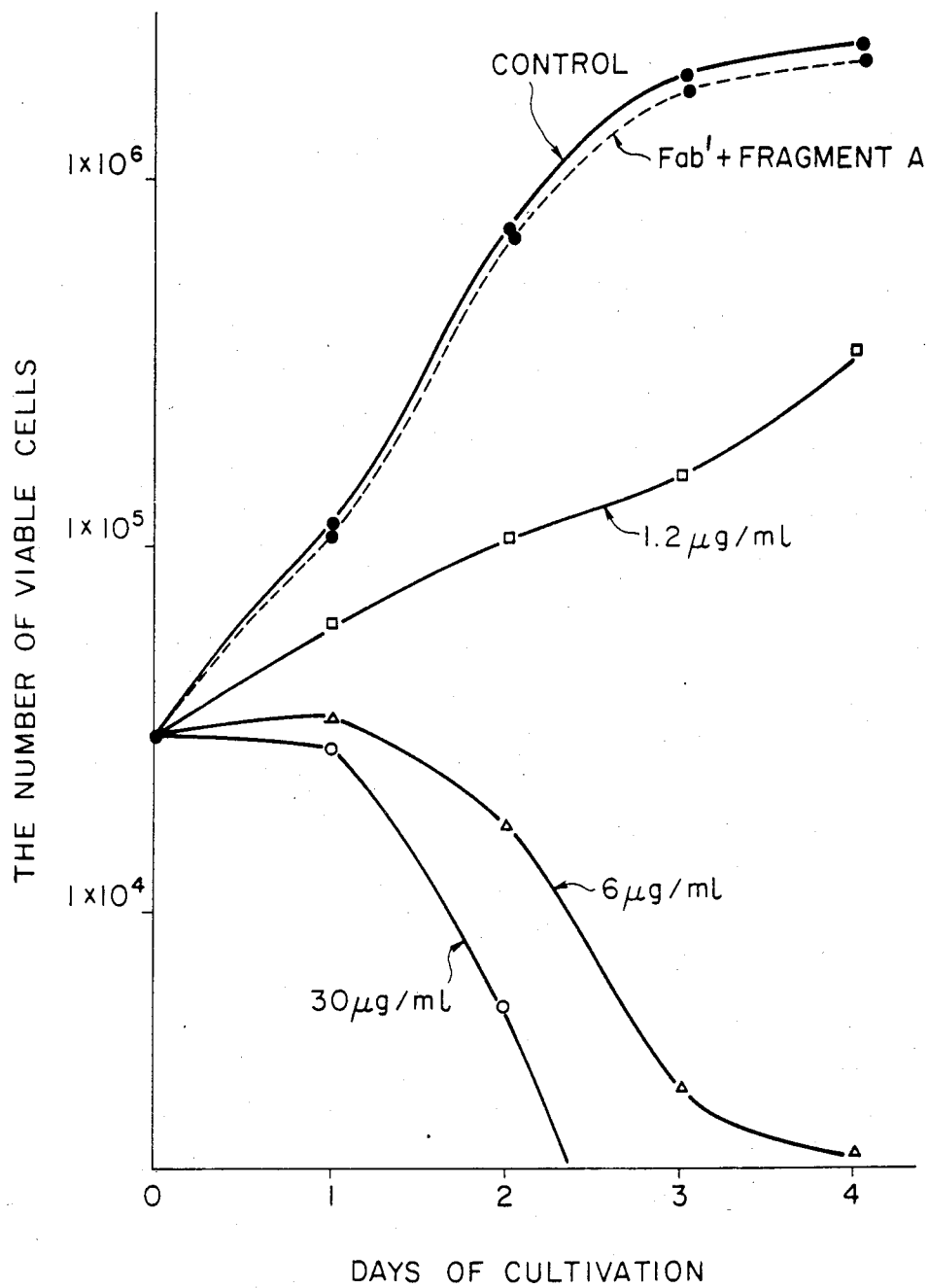
FIG. 7 is a figure to show the result of the measurement of the cytotoxicity of the antitumor protein hybrid against L1210 with the passage of time.

It is clear from FIG. 7 that the antitumor protein hybrid shows a remarkable effect of cytotoxicity at a concentration of 30 and 6 µg/ml. The effect was especially remarkable from the second day of cultivation. On the other hand, no cytotoxicity was observed at all with the mixed solution of fragment Fab' and fragment A of diphtheria toxin mixed at a molar ratio of 1:1 (in which both were not bonded). It is therefore understood that it is necessary for both fragments to be bonded into a hybrid with a covalent bond for the manifestation of toxicity.

EXAMPLE 4

According to Example 3, antitumor protein hybrid was obtained, in which fragment Fab' and fragment A were linked by a cross-linking agent of N,N'-(1,3-phenylene)dimaleimide via the respective sulfur atoms, wherein N,N'-(1,3-phenylene)dimaleimide was used in the place of PDM which was used in Example 3.

EXAMPLE 5

According to Example 3, antitumor protein hybrid was obtained, in which fragment Fab' and fragment A were linked by a cross-linking agent of 4,4'-bis(maleoylamino)azobenzene via the respective sulfur atoms, wherein 4,4'-bis(maleoylamino)azobenzene was used in the place of PDM which was used in Example 3.

EXAMPLE 6

Fragment Fab' of anti-L 1210 immunoglobulin IgG having one thiol radical obtained according to Example 1, (a), was dissolved in a mixed solution consisting of 3 parts by volume of 0.1M sodium phosphate buffer (pH 6.0) and 1 part by volume of N,N-dimethylformamide at a concentration of 7 mg/ml to prepare a solution of fragment Fab'. Besides this solution, a solution was prepared by dissolving a cross-linking agent of N,N'-ethylenebis(iodoacetamide) in N,N-dimethylformamide at a concentration of 6 mg/ml.

The reaction was carried out at room temperature for one hour by adding 0.1 ml of the N,N-ethylenebis(iodoacetamide) solution dropwise to 1.0 ml of the fragment Fab' solution, to which reaction mixture 0.05 ml of 0.07M aqueous solution of 2-mercaptoethylamine was added. The mixture was left standing at room temperature for one hour. The obtained mixed solution was purified by column chromatography on Sephadex G25 equilibrated with 0.1M sodium phosphate buffer (pH 6.0) to give a solution of fragment Fab' having N,N'-ethylenebis(iodoacetamide) residue.

The fragment A of diphtheria toxin having one thiol radical prepared according to Example 2, (b), was added to the solution of fragment Fab' having N,N'-ethylenebis(iodoacetamide) residue obtained as mentioned above to make the molar ratio of fragment Fab' having N,N'-ethylenebis(iodoacetamide) residue to fragment A 1:2 and mixed. After that, the procedures were followed as in the case of Example 3 to give the protein hybrid of the present invention in which fragment Fab' and fragment A were linked by a cross-linking agent of N,N'-ethylenebis(iodoacetamide) through the medium of the respective sulfur atoms. This protein hybrid had almost the same remarkable cytotoxic activity against L 1210 as the one according to Example 1.

EXAMPLE 7

According to Example 6, antitumor protein hybrid was obtained, in which fragment Fab′ and fragment A were linked by a cross-linking agent of N,N′-hexamethylenebis(iodoacetamide) through the medium of the respective sulfur atoms, wherein N,N′-hexamethylenebis(iodoacetamide) was used in the place of N,N′-ethylenebis(iodoacetamide) which was used in Example 6.

EXAMPLE 8

According to Example 6, antitumor protein hybrid was obtained, in which fragment Fab′ and fragment A were linked by a cross-linking agent of N,N′-undecamethylenbis(iodoacetamide) through the medium of the respective sulfur atoms, wherein N,N′-undecamethylenebis(iodoacetamide) was used in place of N,N′-ethylenebis(iodoacetamide) which was used in Example 6.

EXAMPLE 9

According to Example 6, antitumor protein hybrid was obtained, in which fragment Fab′ and fragment A were linked by a cross-linking agent of bis(N-maleimidemethyl)ether through the medium of the respective sulfur atoms, wherein bis(N-maleimidemethyl)ether was used in the place of N,N′-ethylenebis(iodoacetamide) which was used in Example 6.

What is claimed is:

1. Antitumor protein hybrid comprising (1) a moiety which is substantially the fragment Fab of an antitumor immunoglobulin and (2) a moiety which is substantially the fragment A of a diphtheria toxin, which antitumor protein hybrid is expressed by the following formula (I):

$$Fab(-S_1-(X)_n-S_2-FA)_m \qquad (I)$$

where FAB indicates a moiety which is substantially the fragment FAB of an antitumor immunoglobulin; FA indicates a moiety which is substantially the fragment A of a diphtheria toxin; X indicates a divalent organic radical; $S_1$ and $S_2$ are both sulfur atoms, $S_1$ indicating a sulfur atom arising from the disulfide bond in the immunoglobulin and $S_2$ a sulfur atom arising from the disulfide bond in the diphtheria toxin; n represents 0 or 1 and m represents an integer of 1 to 5.

2. Antitumor protein hybrid according to claim 1 which is expressed by the following formula (II):

$$Fab(-S_1-S_2-FA)_p \qquad (II)$$

where the definitions of Fab, FA, $S_1$ and $S_2$ are the same as those given in case of formula (I) and p represents 1 or 2.

3. Antitumour protein hybrid according to claim 1 or claim 2, wherein FA is a moiety derived from the fragment A of the diphtheria toxin.

4. Antitumour protein hybrid according to claim 1 or claim 2, wherein Fab is a moiety derived from the fragment Fab of the antitumour immunoglobulin.

5. Antitumour protein hybrid according to claim 1 or claim 2, wherein Fab is a moiety derived from the fragment Fab′ of the antitumour immunoglobulin.

6. Antitumour protein hybrid according to claim 1, wherein X is a divalent organic radical arising from a bismaleimide compound which is expressed by the following formula (III):

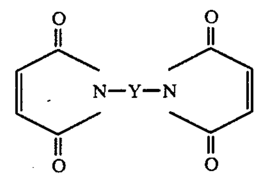

(III)

where Y indicates a divalent organic radical.

7. Antitumour protein hybrid according to claim 1, wherein X is a divalent organic radical arising from a bishalocarbonyl compound which is expressed by the following formula (IV):

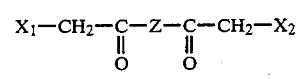

(IV)

where Z indicates a divalent organic radical, and $X_1$ and $X_2$ are either the same or different from each other and represent bromine or iodine.

8. Antitumour protein hybrid according to claim 1, wherein X is a divalent organic radical arising from a dihaloketone compound which is expressed by the following formula (V):

$$X_1-CH_2-CO-CH_2-X_2 \qquad (V)$$

where $X_1$ and $X_2$ are either the same or different from each other and represent bromine or iodine.

9. Antitumour protein hybrid according to claim 1, wherein X is a divalent organic radical arising from a halocarbonyl maleimide compound which is expressed by the following formula (VI):

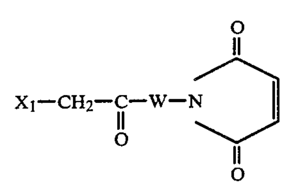

(VI)

where W is a divalent organic radical and X represents bromine or iodine.

* * * * *